(12) United States Patent
Lazic (10) Patent No.: US 10,881,415 B2
(45) Date of Patent: Jan. 5, 2021

(54) SURGICAL CLIP WITH THREE CLAMPING ARMS

(71) Applicant: Peter Lazic GmbH, Tuttlingen (DE)

(72) Inventor: Daniel Lazic, Tuttlingen (DE)

(73) Assignee: PETER LAZIC GMBH, Tuttlingen (DE)

( * ) Notice: Subject to any disclaimer, the term of this patent is extended or adjusted under 35 U.S.C. 154(b) by 208 days.

(21) Appl. No.: 16/258,610

(22) Filed: Jan. 27, 2019

(65) Prior Publication Data

US 2019/0150933 A1 May 23, 2019

Related U.S. Application Data

(63) Continuation-in-part of application No. 14/670,709, filed on Mar. 27, 2015, now Pat. No. 10,226,252.

(30) Foreign Application Priority Data

Apr. 10, 2014 (EP) ..................................... 14164160

(51) Int. Cl.
*A61B 17/122* (2006.01)
*A61B 17/11* (2006.01)

(52) U.S. Cl.
CPC .......... *A61B 17/1227* (2013.01); *A61B 17/11* (2013.01); *A61B 2017/1103* (2013.01); *A61B 2017/1107* (2013.01); *A61B 2017/1132* (2013.01); *A61B 2017/1139* (2013.01)

(58) Field of Classification Search
CPC ....... A61B 17/08; A61B 17/083; A61B 17/11; A61B 17/12; A61B 17/122; A61B 17/1227; A61B 2017/1107; A61B 2017/1121; A61B 2017/1132; A61B 2017/12004; Y10T 24/44325
See application file for complete search history.

(56) References Cited

U.S. PATENT DOCUMENTS

| | | | |
|---|---|---|---|
| 2,416,733 | A | 3/1947 | Berndt |
| 6,517,554 | B1 | 2/2003 | Zhu |
| 8,273,096 | B2 | 9/2012 | Lazic |
| 2002/0111643 | A1 | 8/2002 | Herrmann |
| 2014/0364882 | A1 | 12/2014 | Tulleken et al. |

FOREIGN PATENT DOCUMENTS

| | | |
|---|---|---|
| DE | 203 03 496 U1 | 7/2003 |
| DE | 10 2004 016 859 A1 | 10/2005 |
| DE | 10 2009 003273 A1 | 11/2010 |

*Primary Examiner* — Todd J Scherbel
(74) *Attorney, Agent, or Firm* — Hackler Daghighian Martino & Novak (57) ABSTRACT

A surgical clip includes a spring pretensioning two outer double-armed clip parts and a double-armed clip part rotatably mounted. Each outer double-armed clip part includes one operating arm configured to be pressed together into an open clip position by an applying forceps and one clamping arm. The middle clip part has a clamping arm arranged between the clamping arms of the two outer clip parts and an operating arm arranged between the operating arms of the two outer clip parts. The middle clip part's operating arm is configured to be opened in relation to either of the operating arms of the two outer clip parts by the applying forceps engaging a respective side of the middle clip part's operating arm associated with the operating arm of either of the two outer clip parts to open the middle clip part's clamping arm and the respective middle clip part's clamping arm.

14 Claims, 5 Drawing Sheets

SURGICAL CLIP WITH THREE CLAMPING ARMS

CROSS-REFERENCE TO RELATED APPLICATIONS

This continuation-in-part patent application claims priority to the non-provisional patent application Ser. No. 14/670,709 filed on Mar. 27, 2015, which itself claimed priority to European Patent Application No. 14 164 160.5, filed Apr. 10, 2014, the entire contents of which all applications hereby are incorporated by these references.

FIELD OF THE INVENTION

The invention relates to a surgical clip with clamping arms, which is used for clamping hollow organs, in particular blood vessels, or for connecting two blood vessels.

BACKGROUND OF THE INVENTION

DE 10 2004 016 859 A1 and DE 10 2009 003 273 A1 disclose aneurysm clips with two rotatably mounted clip parts, each of which comprises one operating arm and one clamping arm. A helical or leg spring is arranged in a central opening of the two clip parts, the spring legs of which are welded to the two clip parts in order to pretension the two clip parts into a closed clip position in which the two clamping arms abut one another.

It is the object of the present invention to provide a surgical clip that can be used in a variety of ways and can, in particular, also be used to connect two vessels.

SUMMARY OF THE INVENTION

This object is achieved in accordance with the invention with a surgical clip comprising two outer double-armed clip parts that are mounted to be rotatable about an axis of rotation and each comprise one operating arm configured to be pressed together into an open clip position by an applying forceps and one clamping arm; a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging an a respective side of the operating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another.

In accordance with the invention, the spring only engages on the two outer clip parts such that the middle clip element is mounted between the two outer clip parts such that it can freely rotate. The middle clamping arm and electively one of the two outer clamping arms can be opened with respect to each other by means of an applying forceps that presses together open the middle operating arm and one of the two outer operating arms, wherein the middle clamping arm carries along the other outer clamping arm, which abuts the outside, in an outward direction, namely against the closing force of the spring that acts between the two outer clip parts. While the middle clamping arm and one of the outer clamping arms are opened, the other outer clamping arm is held in abutment on the middle clamping arm, i.e. the middle clamping arm and the other outer clamping arm remain in the closed position. For this reason, a first vessel can be clamped between the middle clamping arm and one of the outer clamping arms and a second vessel can subsequently be clamped between the middle clamping arm and the other outer clamping arm without having to release clamping of the first vessel. As a result, two vessels are simultaneously clamped to the clip.

In one preferred embodiment of the invention, the two outer clip parts each comprise a circular roller section between the operating and clamping arms, and a quarter-circular bearing shell, the roller section and the bearing shell being arranged coaxially to one another with the outer diameter of the roller section and the diameter of the bearing shell being identical, and wherein the middle clip part comprises a circular roller section between the operating and clamping. The axis of rotation is formed by the roller sections and the bearing shells which together form a roller bearing. In this embodiment, the inventive clip thus consists of four individual parts, i.e. the three clip parts and the spring.

In another preferred embodiment of the invention, the three clip parts each comprise a ring with a circular ring opening for forming a common ring opening. The spring, a bearing sleeve or a shaft is inserted in the common ring opening to form a pivot bearing The two spring ends of the spring are preferably connected to the two outer clip parts in a material-bonding manner, in particular through welding. The spring legs can alternatively only be clamped around the outer side of the outer clip parts—similar to the leg spring of a clothespin.

The spring is preferentially designed as a leg spring, the two spring legs of which engage on the two outer clip parts. In case of a bearing sleeve, all coil turns, i.e. the overall spring winding body of the leg spring, are completely arranged within the bearing sleeve, if possible, in order to prevent bruises of tissue between the individual coil turns of the leg spring.

The clamping arms are either designed in one piece with their clamping arm ends or each clamping arm is designed in two pieces with a clamping arm base and a clamping arm end, wherein the clamping arm base has an interface for fastening the clamping arm end.

In one particularly preferred embodiment of the inventive clip, each clamping arm end is designed as a ring, wherein the rings abut each other in the closed clip position and the ring openings, which are in particular of identical size, form a through-hole. This clip is particularly suited for bypass operations, in which two blood vessels are connected to each other. The two vessels must normally be sewed together which requires a large amount of time and great precision of the operating surgeon. The two open vessel ends are each turned inside out over the rings of the outer clip parts and clamped by the ring of the middle clip part, thereby connecting the two vessel ends to each other without sewing.

In another preferred embodiment of the inventive clip, the clamping arms of the two outer clip parts are each designed as a fork and the clamping arm of the middle clip part is designed as a ring, which enables connection of two vessel walls to each other.

In a further preferred embodiment of the inventive clip, the clamping arm of one of the two outer clip parts is designed as a fork and the clamping arms of the other two clip parts are each designed as a ring, which enables connection of one vessel end to one vessel wall.

The invention enables a method for connecting two vessels, in particular two blood vessels, by means of the above-described surgical clips.

The invention also enables a method for connecting the open vessel ends of two vessels by means of the above-described surgical clip.

The invention also enables a method for connecting a vessel wall and a vessel end by means of the above-described surgical clip.

These methods considerably facilitate connection of two vessels, in particular, in bypass operations. After fixing of the first vessel, the second vessel can subsequently be fixed without thereby having to release the connection of the first vessel. The two open vessel ends are each clamped by the ring of the middle clip part after turning them inside out over the rings of the outer clip parts, thereby connecting the two vessel ends to each other without sewing.

Further advantages of the invention can be extracted from the description, the claims and the drawing. The features mentioned above and below may be used individually or collectively in arbitrary combination. The embodiments illustrated and described are not to be understood as exhaustive enumeration but have exemplary character for describing the invention.

BRIEF DESCRIPTION OF THE DRAWINGS

The accompanying drawings illustrate the invention. In such drawings.

DETAILED DESCRIPTION OF THE PREFERRED EMBODIMENTS

In the following description of the drawing, identical components or components having identical functions are designated by the same reference numerals.

Figure 1A:
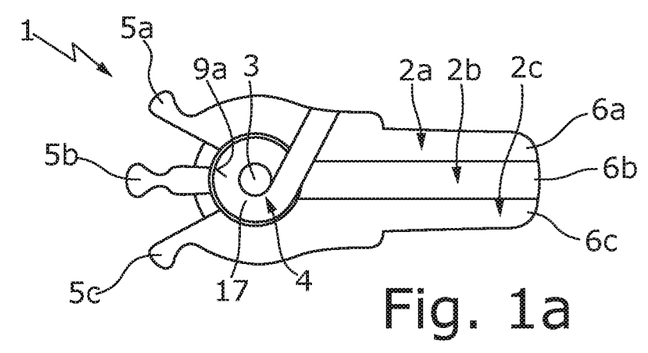
FIGS. 1a-1c show an inventive surgical clip comprising three rotatably mounted double-armed clip parts in a closed clip position (FIG. 1a), in a first open clip position (FIG. 1b), and in a second open clip position (FIG. 1c)

The surgical clip 1 shown in FIG. 1a comprises three double-armed clip parts 2a, 2b, 2c, which are connected to each other such that they can be rotated about an axis of rotation 3 and are pretensioned by a leg spring 4 into their closed clip position shown in FIG. 1a.

The double-armed clip parts 2a, 2b, 2c each have a short operating arm 5a, 5b, 5c and a long clamping arm 6a, 6b, 6c. The operating arm 5b of the middle clip part 2b is arranged between the operating arms 5a, 5c of the two outer clip parts 2a, 2c, and its clamping arm 6b is arranged between the clamping arms 6a, 6c of the two outer clip parts 2a, 2c. The operating and clamping arms 5a, 6a and respectively 5c, 6c of each outer clip part 2a, 2c are disposed on the same side with respect to the axis of rotation 3. The two spring legs 7 of the leg spring 4 are welded to the two outer clamping arms 6a, 6c, the leg spring 4 thereby pretensioning the two outer clip parts 2a, 2c into the closed clip position, in which the clamping arms 6a, 6b, 6c abut each other.

The middle clamping arm 6b and the associated outer clamping arm 6a or 6c can each be opened relative to each other against the closing force of the leg spring 4 by means of an applying forceps (not shown) which presses together the middle operating arm 5b and one of the two outer operating arms 5a or 5c to open them. To be more precise, the middle clamping arm 6b carries along the abutting other outer clamping arm 6c or 6a in its opening direction during opening, i.e. against the closing force of the leg spring 4 that acts on the other outer clamping arm 6c or 6a.

Figure 1B:
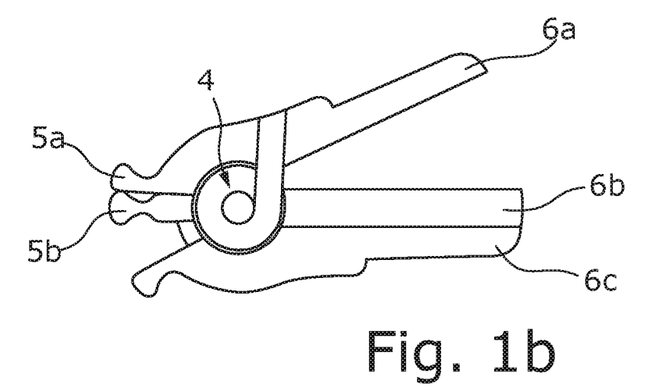
Figure 1C:
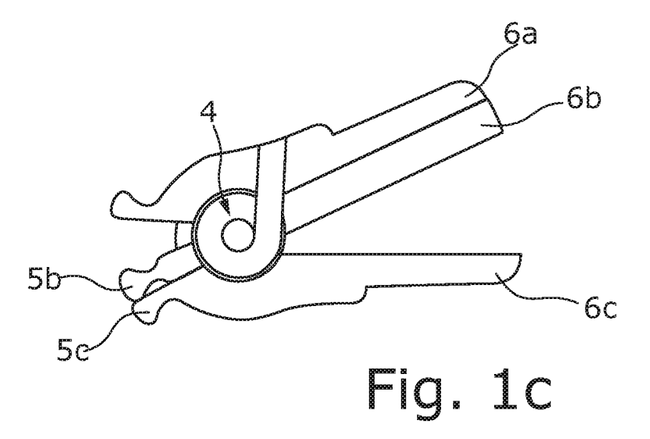
Figure 2A:
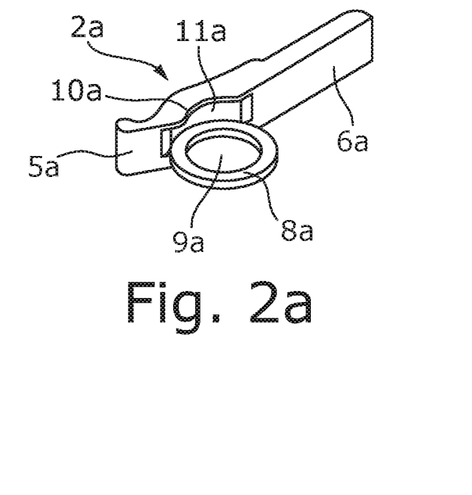
FIGS. 2a, 2b show the one outer clip part of the clip shown in FIG. 1 in perspective view (FIG. 2a) and in axial top view (FIG. 2b)
Figure 2B:
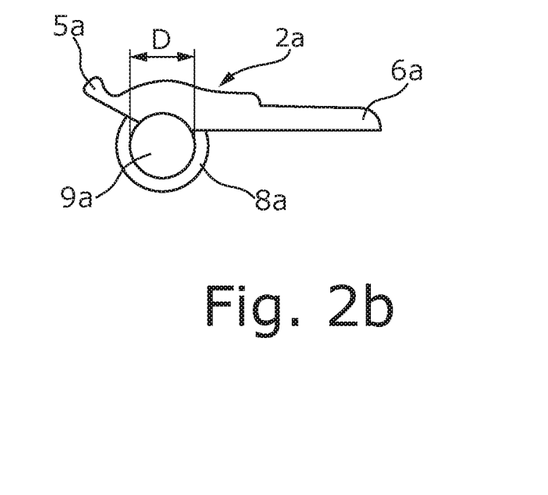

In FIG. 1b, the middle operating arm 5b and the upper outer operating arm 5a are pressed together and for this reason, the middle clamping arm 6b and the upper outer clamping arm 6a are open with respect to each other. The lower outer clamping arm 6c that abuts the middle clamping arm 6b is carried along in the opening direction by the middle clamping arm 6b against the closing force of the leg spring 4. In FIG. 1c, the middle operating arm 5b and the lower outer operating arm 5c are pressed together, thereby opening the middle clamping arm 6b and the lower outer clamping arm 6c with respect to each other. The upper outer clamping arm 6a that abuts the middle clamping arm 6b is thereby carried along in the opening direction by the middle clamping arm 6b against the closing force of the leg spring 4.

Figure 3A:
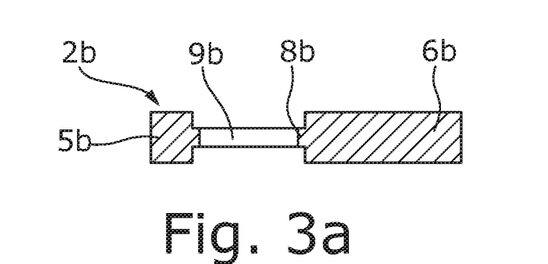
FIGS. 3a, 3b show the middle clip part of the clip shown in FIG. 1 in side view (FIG. 3a) and in axial top view (FIG. 3b)
Figure 3B:
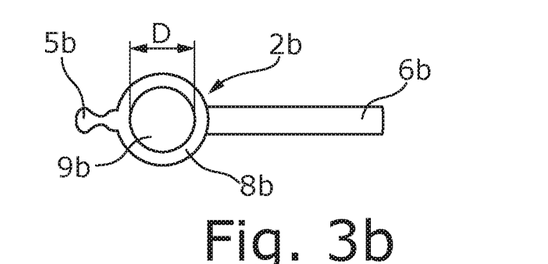
Figure 4A:
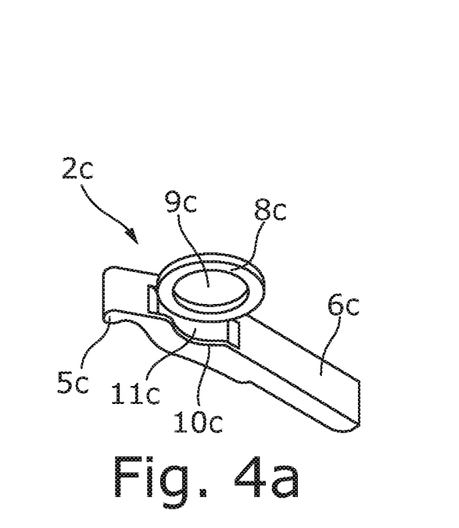
FIGS. 4a, 4b show the other outer clip part of the clip shown in FIG. 1 in perspective view (FIG. 4a) and in axial top view (FIG. 4b)
Figure 4B:
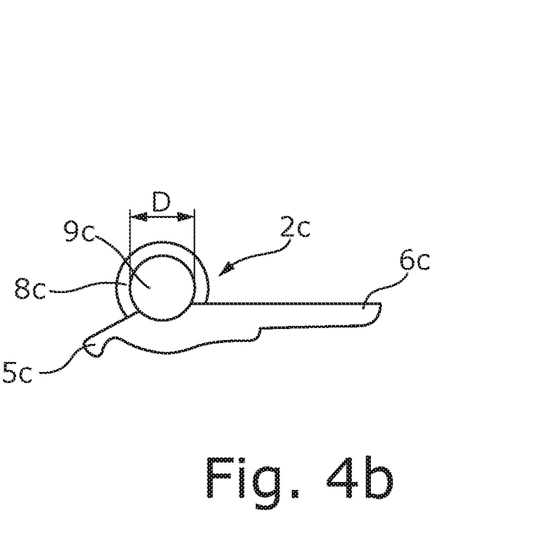

As is shown in FIGS. 2a, 2b and 4a, 4b, the two outer clip parts 2a, 2c are identical and each have a roller section designed as a circular ring 8a, 8c with a circular ring opening 9a, 9b (opening diameter D) between the operating and clamping arms 5a, 6a and 5c, 6c, respectively. The ring 8a, 8c is provided at one of the two axial end faces of the clip part 2a, 2c, and a protrusion 10a, 10c which protrudes radially inward is provided at the other axial end face of the clip part 2a, 2c. The two outer clip parts 2a, 2c each have a quarter-circular bearing shell 11a, 11b provided axially between the ring 8a, 8c and the protrusion 10a, 10c. The ring 8a, 8c and the bearing shell 11a, 11b are arranged coaxially to one another with the outer diameter of the ring 8a, 8c and the diameter of the bearing shell 11a, 11b being identical. As is shown in FIGS. 3a and 3b, the middle clip part 2b also has a roller section designed as a circular ring 8b with a circular ring opening 9b (opening diameter D) between the operating and clamping arms 5b, 6b.

For assembling the clip 1, the rings 8a-8c of the clip parts 2a-2c are placed on top of each other with the ring 8b of the middle clip part 2b being sandwiched between the rings 8a, 8c of the two outer clip parts 2a, 2c. The ring openings 9a-9c form a common ring opening. As a result, the ring of one outer clip part and the ring 8b of the middle clip part 2b are precisely fitted between the ring and the protrusion of the other outer clip part. The spring winding body 17 (FIG. 1a) of the leg spring 4 is finally fitted into the common ring opening and is then welded with its two spring legs 7 to the outer side of the clamping arms 6a, 6c with pretension in order to pretension the clip parts 2a, 2c already in their closed clip position. The axis 3 of rotation is formed by the rings 8a-8c and the bearing shells 10a-10c which together form a roller bearing. In this embodiment, the clip 1 thus consists of four individual parts, i.e. the three clip parts 2a, 2b, 2c and the spring 4 which holds together the clip parts.

Instead of bearing shells, the pivot bearing can also be formed by a sleeve or a solid bearing shaft the outer diameter of which corresponds to the diameter of the ring opening D. The sleeve or shaft is inserted in the common ring opening to form a pivot bearing. In case of a sleeve, the spring winding body 17 of the leg spring 4 is finally fitted into the sleeve and is then welded with its two spring legs 7 to the outer side of the clamping arms 6a, 6c with pretension in order to pretension the clip parts 2a, 2c already in their closed clip position. In case of a shaft, however, the spring winding body 17 must be arranged on the outside of the clip 1. In this embodiment, the clip 1 thus consists of five individual parts, i.e. the three clip parts 2a, 2b, 2c, the bearing sleeve or shaft and the spring 4.

In an embodiment, which is not shown, without bearing shells, the spring winding body 17 of the leg spring 4, the round outer diameter of which corresponds in this case to the opening diameter D of the circular ring openings except for a minimum bearing play, is inserted through the ring openings 9a, 9b, 9c. The leg spring 4 thus forms the pivot bearing about which all three clip parts rotate. In this embodiment, the clip 1 thus consists of four individual parts, i.e. the three clip parts 2a, 2b, 2c and the leg spring 4.

Instead of welding the spring legs 7 to the clip parts 2a, 2c, the two spring legs 7 can alternatively be clamped around the outer side of the clamping arms 6a, 6c—similar to a clothespin. In this case, the two clip parts 2a, 2b, 2c can also be formed from non-weldable material such as e.g. plastic material, in particular from polymethylmethacrylate (PMMA) or from X-ray transparent polyetheretherketone (PEEK). In case of the separate bearing sleeve 10, the sleeve ends can e.g. be radially bent to the outside in order to undetachably mount the clip parts on the bearing sleeve 10.

Figure 5:
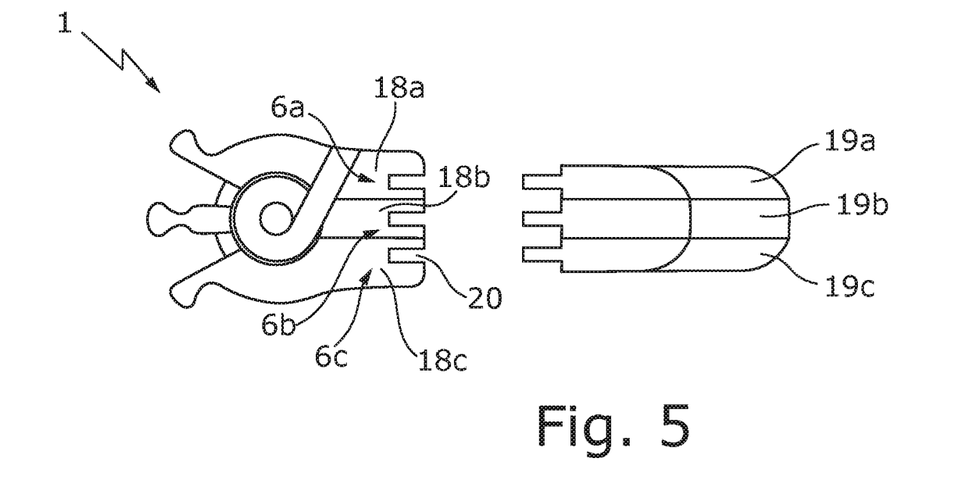
FIG. 5 shows an inventive surgical clip with clamping arms designed in two pieces.

The clip 1 shown in FIG. 5 differs from the clip 1 of FIG. 1 only in that the clamping arms 6a, 6b, 6c therein are each formed in two parts having a clamping arm base 18a, 18b, 18c and a clamping arm end 19a, 19b, 19c. The clamping arm base 18a, 18b, 18c has an interface 20 which is designed e.g. as a receiving area for optionally mounting different clamping arm ends 19a, 19b, 19c.

Figure 6:
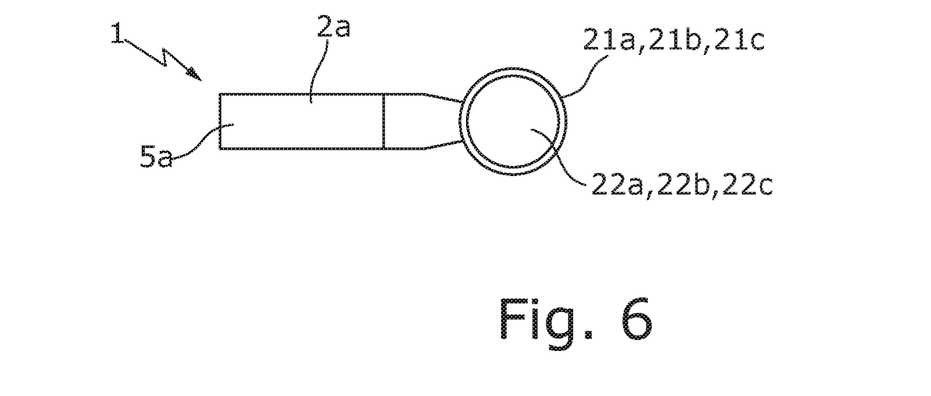
FIG. 6 shows an inventive surgical clip with annular clamping arms.

In the surgical clip 1 shown in FIG. 6, the clamping arm ends are formed in each case as rings 21a, 21b, 21c with identically sized ring openings 22a, 22b, 22c, which abut each other in the closed clip position and the ring openings 22a, 22b, 22c of which coincide to thereby form a through opening.

FIGS. 7a-7d show the individual method steps for connecting two vessels (e.g. blood vessels) 23, 24 by means of the surgical clip 1 shown in FIG. 11.

Figure 7A:
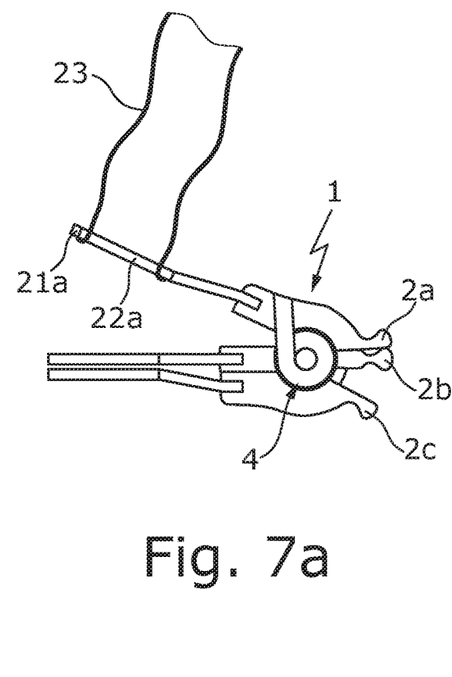
FIGS. 7a-7d show the individual method steps for connecting two vessels by means of the surgical clip shown in FIG. 6.

In FIG. 7a, the clip 1 is opened by closing the first outer clip part 2a and the middle clip part 2b and the open vessel end of the first blood vessel 23 is guided through the annular opening 22a of the first outer clip part 2a and then turned inside out around the ring 21a of the first outer clip part 2a.

Figure 7B:
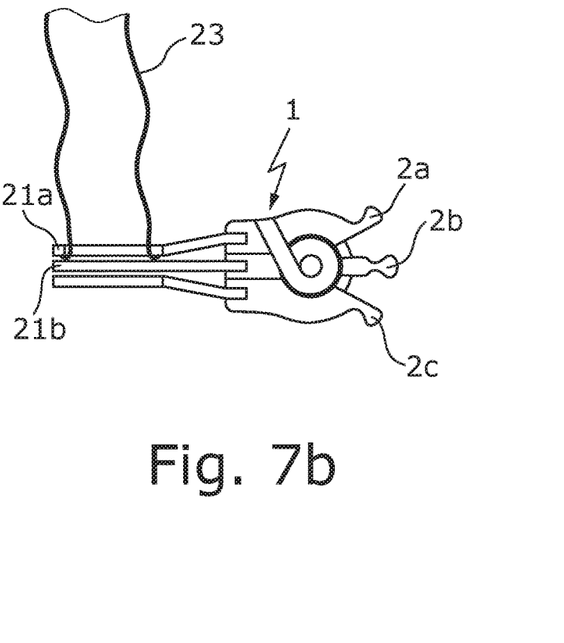

In FIG. 7b, the clip 1 is closed again, thereby clamping the vessel end, which is turned inside out, between the rings 21a, 21b of the first outer clip part 2a and of the middle clip part 2b by the closing force of the leg spring 4.

Figures 7C, 7D:
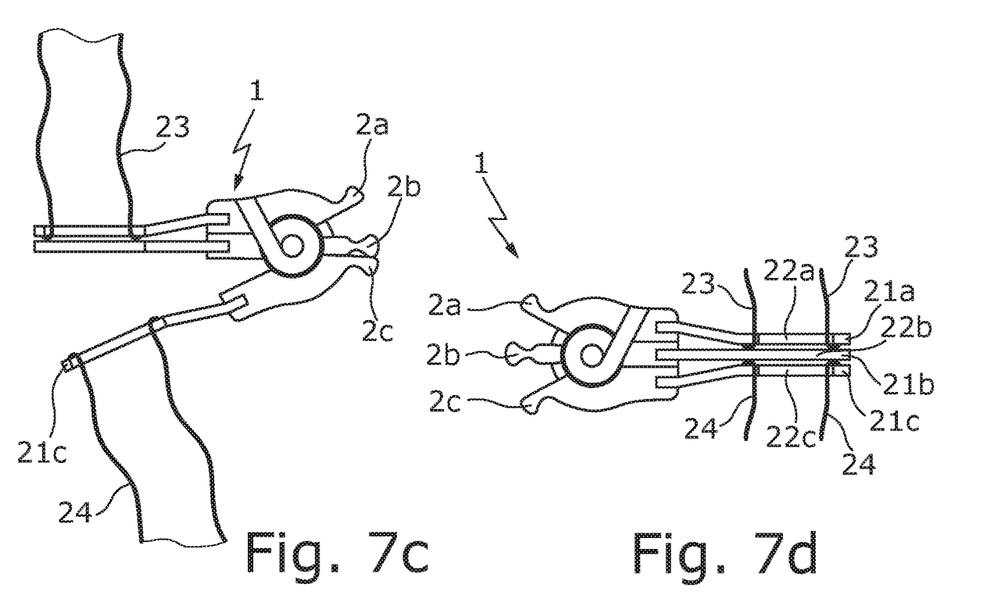

In FIG. 7c, the clip 1 is opened by closing the second outer clip part 2c and the middle clip part 2b and the open vessel end of the second blood vessel 24 is guided through the annular opening 22c of the second outer clip part 2c and then turned inside out around the ring 21c of the second outer clip part 2c.

In FIG. 7d, the clip 1 is closed again, thereby clamping the vessel end, which is turned inside out, of the second blood vessel 24 between the rings 21c, 21b of the second outer clip part 2c and of the middle clip part 2b. The open vessel ends of the two blood vessels 23, 24, which have been turned inside out over the rings 21a, 21c of the outer clip parts 2a, 2c, are clamped by the ring 21b of the middle clip part 2b and connected to each other without sewing.

Figure 8A:
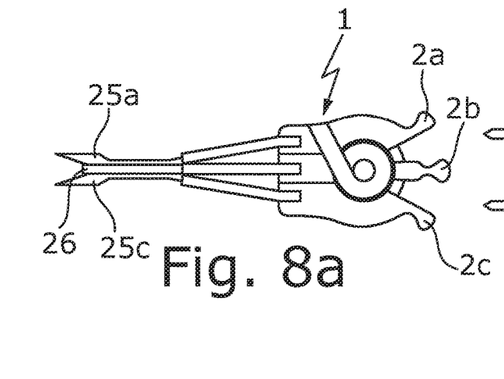
FIGS. 8a-8b show a further inventive surgical clip with an annular middle clamping arm and two double-pin-shaped outer clamping arms in side view (FIG. 8a) and in axial top view (FIG. 8b)
Figure 8B:
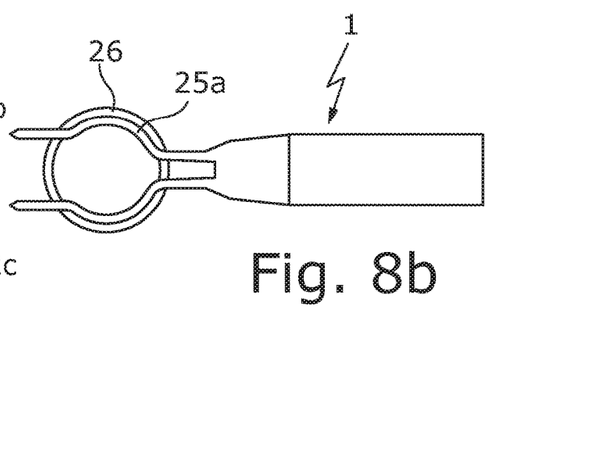

The clamping arm ends of the two outer clip parts 2a, 2c of the surgical clip 1 shown in FIGS. 8a, 8b, are each designed as a fork (double needle) 25a, 25c and the clamping arm end of the middle clip part 2b is designed as a ring 26. The forks 25a, 25c each have central sections that are bulged to the outside in a circular shape and abut the ring 26 of the middle clip part 2b in the closed clip position.

FIGS. 9a-9d show the individual method steps for connecting two blood vessels 23, 24 by means of the surgical clip 1 shown in FIG. 8.

Figure 9A:
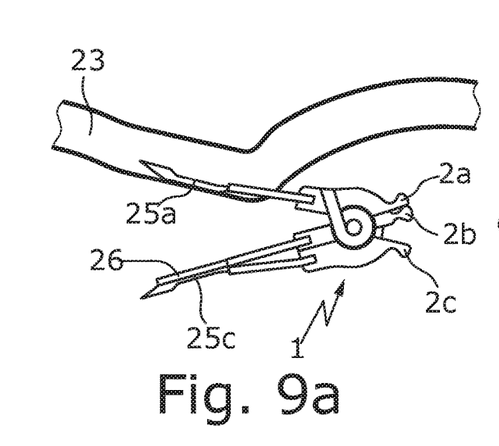
FIGS. 9a-9d show the individual method steps for connecting two vessels by means of the surgical clip shown in FIG. 8.

In FIG. 9a, the clip 1 is opened by closing the first outer clip part 2a and the middle clip part 2b and the fork 25a of the first outer clip part 2a is pierced into the vessel wall of the first blood vessel 23.

Figure 9B:
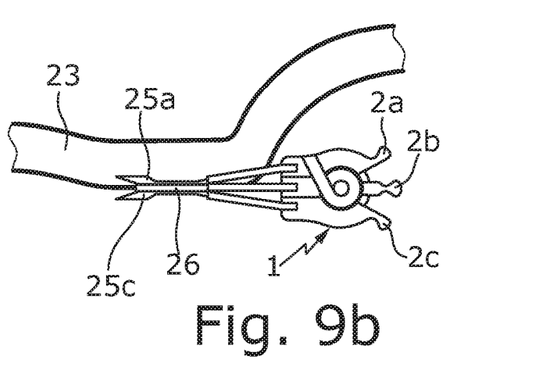

In FIG. 9b, the clip 1 is closed again, thereby clamping the pierced vessel wall between the fork 25a of the first outer clip part 2a and the ring 26 of the middle clip part 2b by the closing force of the leg spring 4.

Figure 9C:
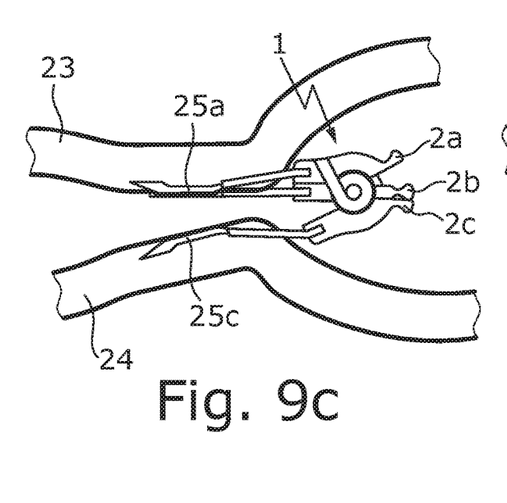

In FIG. 9c, the clip 1 is opened by closing the second outer clip part 2a and the middle clip part 2b and the fork 25c of the second outer clip part 2c is pierced into the vessel wall of the second blood vessel 24.

Figure 9D:
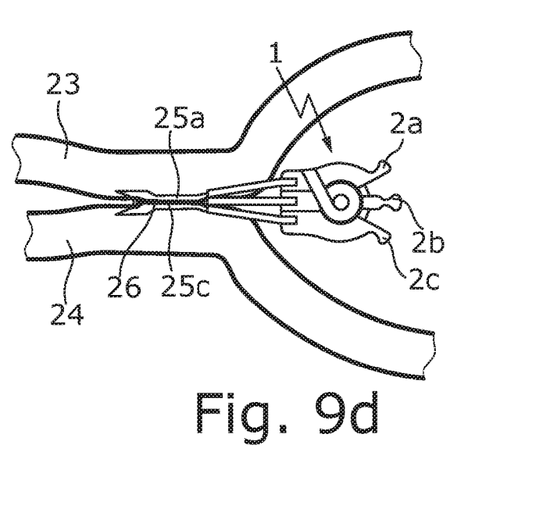

In FIG. 9d, the clip 1 is closed again, thereby clamping the pierced first blood vessel 23 between the fork 25a and the ring 26 and clamping the pierced second blood vessel 24 between the fork 25c and the ring 26. The two vessel walls are finally opened within the ring 26, thereby connecting the two blood vessels 23, 24 to each other.

In one embodiment, which is not shown, the clamping arm of one of the two outer clip parts is designed as a fork and the clamping arms of the other two clip parts are each designed as a ring in order to clamp the vessel end of a first blood vessel between the two rings and also clamp the pierced vessel wall of a second blood vessel between a ring and the fork. The pierced vessel wall is finally opened within the ring, thereby connecting the two blood vessels 23, 24 to each other.

Although several embodiments have been described in detail for purposes of illustration, various modifications may be made to each without departing from the scope and spirit of the invention. Accordingly, the invention is not to be limited, except as by the appended claims.

What is claimed is:

1. A surgical clip, comprising:
two outer double-armed clip parts that are mounted to be rotatable about an axis of rotation and each comprise one operating arm configured to be pressed together into an open clip position by an applying forceps and one clamping arm;
a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the operating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the two outer clip parts each comprise a circular roller section between the operating and clamping arms, and a quarter-circular bearing shell, the roller section and the bearing shell being arranged coaxially to one another with an outer diameter of the roller section and a diameter of the bearing shell being identical, and wherein the middle clip part comprises a circular roller section between the operating and clamping arms.

2. The surgical clip according to claim 1, wherein the roller sections of the two outer clip parts are each provided at one of two axial end faces of each outer clip part, wherein a protrusion which protrudes radially inward is provided at the other axial end face of each outer clip part, and wherein the roller section of one outer clip part and the roller section of the middle clip part are precisely fitted between the roller section and the protrusion of the other outer clip part.

3. The surgical clip according to claim 1, wherein the roller sections of the outer clips parts and the middle clip part are each formed as a circular ring with a ring opening.

4. The surgical clip according to claim 1, wherein two spring ends of the spring are connected to the two outer clip parts in a material-bonding manner.

5. The surgical clip according to claim 1, wherein two spring ends of the spring are connected to the two outer clip parts through welding.

6. The surgical clip according to claim 1, wherein the spring is designed as a leg spring, the winding body of which is at least partially accommodated in a common opening of each of the outer clips parts and the middle clip part.

7. The surgical clip according to claim 1, wherein the clamping arms of the outer clip parts and the middle clip part are designed in one piece with their clamping arm ends.

8. The surgical clip according to claim 1, wherein the clamping arms of each of the outer clip parts and the middle clip part are designed in each case in two parts with a clamping arm base and a clamping arm end, and each clamping arm base comprises an interface for fixing each clamping arm end.

9. The surgical clip according to claim 1, wherein the clamping arms of the outer clip parts and the middle clip part are designed in each case as rings that abut each other in the closed clip position and ring openings of which form a through-hole.

10. A surgical clip, comprising:
two outer double-armed clip parts that are mounted to be rotatable about an axis of rotation and each comprise one operating arm configured to be pressed together into an open clip position by an applying forceps and one clamping arm;

a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the operating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the three clip parts each comprise a ring with a circular ring opening for forming a common ring opening and wherein the spring, a bearing sleeve or a shaft is inserted in the common ring opening to form a pivot bearing.

11. A surgical clip, comprising:
two outer double-armed clip parts that are mounted to be rotatable about an axis of rotation and each comprise one operating arm configured to be pressed together into an open clip position by an applying forceps and one clamping arm;

a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the operating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the spring is designed as a leg spring, the winding body of which is at least partially accommodated in a common opening of the three clip parts.

12. The surgical clip according to claim 1, wherein the clamoing arm of one of the two outer clip parts is designed as a fork and the clamping arms of the other two clips parts are each designed as a ring.

13. A surgical, comprising:
two outer double-armed clip parts that are mounted to be rotatable about an axis of rotation and each comprise one operating arm configured to be pressed together into an open clip position by an applying forceps and one clamping arm;

a double-armed middle clip part that is mounted to be rotable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the oprating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the three clip parts each comprise a ring with a circular ring opening for forming a common ring opening and wherein the spring, a bearing sleeve or a shaft is inserted in the common ring opening to form a pivot bearing.

14. A surgical, comprising:

two outer double-armed clip parts that are mounted to be rotatable about an axis of rotation and each comprise one operating arm configured to be pressed together into an open clip position by an applying forceps and one clamping arm;

a double-armed middle clip part that is mounted to be rotable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the oprating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the spring is designed as a leg spring, the winding body of which is at least partially accommodated in a common opening of the three clip parts.

* * * * *

UNITED STATES PATENT AND TRADEMARK OFFICE
CERTIFICATE OF CORRECTION

PATENT NO. : 10,881,415 B2
APPLICATION NO. : 16/258610
DATED : January 5, 2021
INVENTOR(S) : Daniel Lazic Page 1 of 3

It is certified that error appears in the above-identified patent and that said Letters Patent is hereby corrected as shown below:

In the Claims

Column 6, Line 60-Column 10, Lines 1-26, should read:

1. A surgical clip, comprising:
    two outer double-armed clip parts that are mounted to be rotatable about an axis of rotation and each comprise one operating arm configured to be pressed together into an open clip position by an applying forceps and one clamping arm;
    a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the operating arm of the middle clip part associated with the operating arm of either of the two outer clip parts in order to open the clamping arm of the middle clip part in relation to either of the clamping arms of the two outer clip parts, respectively; and
    a spring pretensioning the two outer clip parts into a closed clip position in which the clamping arms of the two outer clip parts and the middle clip part abut one another;
    wherein the two outer clip parts each comprise a circular roller section between the operating and clamping arms, and a quarter-circular bearing shell, the roller section and the bearing shell being arranged coaxially to one another with an outer diameter of the roller section and a diameter of the bearing shell being identical, and wherein the middle clip part comprises a circular roller section between the operating and clamping arms.

2. The surgical clip according to claim 1, wherein the roller sections of the two outer clip parts are each provided at one of two axial end faces of each outer clip part, wherein a protrusion which protrudes radially inward is provided at the other axial end Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office* face of the outer clip part, and wherein the roller section of one outer clip part and the roller section of the middle clip part are precisely fitted between the roller section and the protrusion of the each outer clip part.

3. The surgical clip according to claim 1, wherein the roller sections of the three clip parts are each formed as a circular ring with a ring opening.

4. The surgical clip according to claim 1, wherein the three clip parts each comprise a ring with a circular ring opening for forming a common ring opening and wherein the spring, a bearing sleeve or a shaft is inserted in the common ring opening to form a pivot bearing.

5. The surgical clip according to claim 1, wherein two spring ends of the spring are connected to the two outer clip parts in a material-bonding manner.

6. The surgical clip according to claim 1, wherein two spring ends of the spring are connected to the two outer clip parts through welding.

7. The surgical clip according to claim 1, wherein the spring is designed as a leg spring, the winding body of which is at least partially accommodated in a common opening of the three clip parts.

8. The surgical clip according to claim 1, wherein the clamping arms of the outer clip part and the middle clip part are designed in one piece with their clamping arm ends.

9. The surgical clip according to claim 1, wherein the clamping arms of the outer clip part and the middle clip part are designed in each case in two parts with a clamping arm base and a clamping arm end, and the clamping arm base comprises an interface for fixing the clamping arm end.

10. The surgical clip according to claim 1, wherein the clamping arms of the outer clip part and the middle clip part are designed in each case as rings that abut each other in the closed clip position and the ring openings of which form a through-hole.

11. The surgical clip according to claim 1, wherein the clamping arms of the two outer clip parts are each designed as a fork and the clamping arm of the middle clip part is designed as a ring.

12. The surgical clip according to claim 1, wherein the clamping arm of one of the two outer clip parts is designed as a fork and the clamping arms of the other two clip parts are each designed as a ring.

13. A surgical clip, comprising:
   two outer double-armed clip parts that are mounted to be rotatable about an axis of rotation and each comprise one operating arm configured to be pressed together into an open clip position by an applying forceps and one clamping arm;

a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the operating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the three clip parts each comprise a ring with a circular ring opening for forming a common ring opening and wherein the spring, a bearing sleeve or a shaft is inserted in the common ring opening to form a pivot bearing.

14. A surgical clip, comprising:

two outer double-armed clip parts that are mounted to be rotatable about an axis of rotation and each comprise one operating arm configured to be pressed together into an open clip position by an applying forceps and one clamping arm;

a double-armed middle clip part that is mounted to be rotatable about the axis of rotation of the two outer double-armed clip parts, wherein the middle clip part comprises a clamping arm arranged between the clamping arms of the two outer clip parts and an operating arm arranged between the operating arms of the two outer clip parts, wherein the operating arm of the double-armed middle clip part is configured to be closed in relation to either of the operating arms of the two outer clip parts by the applying forceps engaging a respective side of the operating arm of the middle clip part associated with the operating arm of either of the two outer clip parts in order to open the clamping arm of the middle clip part in relation to either of the clamping arms of the two outer clip parts, respectively; and a spring pretensioning the two outer clip parts into a closed clip position in which the clamping arms of the two outer clip parts and the middle clip part abut one another;

wherein the spring is designed as a leg spring, the winding body of which is at least partially accommodated in a common opening of the three clip parts.